United States Patent
Delmas

(10) Patent No.: US 12,077,442 B2
(45) Date of Patent: Sep. 3, 2024

(54) METHOD AND A POWER PLANT FOR ON-DEMAND PRODUCING ELECTRICITY FROM NON-FOSSIL POWER SOURCES AND FROM A RENEWABLE LIGNOCELLULOSIC BIOMASS FEEDSTOCK

(71) Applicant: Société BIOEB, Auzeville-Tolosane (FR)

(72) Inventor: Michel Delmas, Auzeville-Tolosane (FR)

(73) Assignee: Société Bioeb, Auzeville-Tolosane (FR)

( * ) Notice: Subject to any disclaimer, the term of this patent is extended or adjusted under 35 U.S.C. 154(b) by 786 days.

(21) Appl. No.: 16/969,724

(22) PCT Filed: Feb. 12, 2019

(86) PCT No.: PCT/EP2019/053379
§ 371 (c)(1),
(2) Date: Aug. 13, 2020

(87) PCT Pub. No.: WO2019/158500
PCT Pub. Date: Aug. 22, 2019

(65) Prior Publication Data
US 2021/0003073 A1  Jan. 7, 2021

(30) Foreign Application Priority Data
Feb. 16, 2018  (EP) .................... 18157086

(51) Int. Cl.
*C01B 32/50* (2017.01)
*C05D 7/00* (2006.01)
(Continued)

(52) U.S. Cl.
CPC ............. *C01B 32/50* (2017.08); *C05D 7/00* (2013.01); *C07C 1/12* (2013.01); *C07C 29/1518* (2013.01);
(Continued)

(58) Field of Classification Search
CPC .................................... F02C 6/02; F02C 7/22
See application file for complete search history.

(56) References Cited

U.S. PATENT DOCUMENTS

| | | | |
|---|---|---|---|
| 7,402,224 B1 * | 7/2008 | Avignon | D21C 5/00 |
| | | | 162/37 |
| 2011/0113778 A1 * | 5/2011 | Bronicki | F03G 6/04 |
| | | | 60/641.14 |

(Continued)

FOREIGN PATENT DOCUMENTS

WO  2011026243 A1  3/2011

OTHER PUBLICATIONS

Shorek-Oslkowskie et al. (Journal of Power Technologies 96(2), 2016, 73-80) (Year: 2016).*

(Continued)

*Primary Examiner* — Liam J Heincer
(74) *Attorney, Agent, or Firm* — Greer, Burns & Crain, Ltd.

(57) ABSTRACT

A method and a power plant for on-demand producing electricity from Non-Fossil Power Sources and from a Renewable Lignocellulosic Biomass Feedstock, in a power plant using several electrical production facilities comprising a first facility for producing electricity from a Non-Fossil Power Source chosen from among wind power, hydro power, solar power, geothermal power and/or tidal power; and a second facility using synthetic gas produced during a gasification step of several fractions from renewable lignocellulosic biomass feedstock obtained by the implementation of an organosolv process using a mixture composed of at least water and formic acid.

4 Claims, 4 Drawing Sheets

(51) Int. Cl.

| | |
|---|---|
| *C07C 1/12* | (2006.01) |
| *C07C 29/151* | (2006.01) |
| *C07C 51/15* | (2006.01) |
| *C07G 1/00* | (2011.01) |
| *C08B 37/00* | (2006.01) |
| *C10J 3/72* | (2006.01) |
| *F02C 6/02* | (2006.01) |
| *F02C 7/22* | (2006.01) |

(52) U.S. Cl.
CPC ............... *C07C 51/15* (2013.01); *C07G 1/00* (2013.01); *C08B 37/0057* (2013.01); *C10J 3/72* (2013.01); *F02C 7/22* (2013.01); *C10J 2300/0916* (2013.01); *C10J 2300/092* (2013.01); *F02C 6/02* (2013.01)

(56) References Cited

U.S. PATENT DOCUMENTS

| | | | |
|---|---|---|---|
| 2012/0202260 A1* | 8/2012 | Maclachlan | C10J 3/00 435/157 |
| 2013/0183733 A1 | 7/2013 | Delmas et al. | |
| 2014/0283439 A1* | 9/2014 | Hitchingham | C10J 3/62 44/605 |
| 2015/0315502 A1* | 11/2015 | Foody | C10J 3/82 518/703 |
| 2018/0023007 A1* | 1/2018 | Bartek | C10G 27/10 435/167 |
| 2021/0002824 A1* | 1/2021 | Delmas | D21H 11/02 |
| 2021/0079123 A1* | 3/2021 | Benjelloun Mlayah | C13K 1/02 |
| 2022/0325187 A1* | 10/2022 | Delmas | C10G 2/32 |

OTHER PUBLICATIONS

Ma et al. (International Journal of Biological Macromolecules 182, 2021, 51-58) (Year: 2021).*
International Search Report; priority document.
Özdencki et al., "A Novel Biorefinery Integration Concept for Lignocellulosic Biomass" Energy Conversion and Management, vol. 149, Apr. 17, 2017, pp. 974-987.
Laosiripojana et al., "Fractionation of Lignin from Lignocellulosic Biomass and its Catalytic Depolymerization to Phenolic Monomers" PACCON 2017.
Li et al., "Sequential Two-Step Fractionation of Lignocellulose with Formic Acid Organosoly Followed by Alkaline Hydrogen Peroxide under Mild Conditions to Prepare Easily Saccharified Cellulose and Value-Added Lignin" Energy Conversion and Management, vol. 148, 2017, pp. 1426-1437.
Zhang et al., "Organosoly Pretreatment of Plant Biomass for Enhanced Enzymatic Saccharification" vol. 18, 2016, pp. 360-381.
De Wild, et al., "Organosoly Fractionation of Lignocellulosic Biomass for an Integrated Biorefinery" vol. 1, Feb. 2015, pp. 10-11.
Gu et al., "Life-Cycle GHG Emissions of Electricity from Syngas Prodoced by Pyrolyzing Woody Biomass" Proceedings of the 58th International Convention of Society of Wood Science and Technology, Jun. 2015, pp. 376-389.
Skorek-Osikowska et al., "Use of a Gas Turbine in a Hybrid Power Plant Integrated with an Electrolyser, Biomass Gasification Generator and Methanation Reactor" Journal of Power Technologies, vol. 96, 2016, pp. 73-80.
Yue et al, "Thermodynamic Analysis of Solar-Assisted hybrid Power Generation Systems Integrated with Thermochemical Fuel Conversion" ENERGY, vol. 118, 2017, pp. 671-683.

* cited by examiner

METHOD AND A POWER PLANT FOR ON-DEMAND PRODUCING ELECTRICITY FROM NON-FOSSIL POWER SOURCES AND FROM A RENEWABLE LIGNOCELLULOSIC BIOMASS FEEDSTOCK

CROSS-REFERENCES TO RELATED APPLICATIONS

This application claims the benefit of the International Application No. PCT/EP2019/053379, filed on Feb. 12, 2019, and of the European patent application No. 18157086.2 filed on Feb. 16, 2018, the entire disclosures of which are incorporated herein by way of reference.

FIELD OF THE INVENTION

The invention relates to a method for on-demand producing electricity from non-fossil power sources and from a renewable lignocellulosic biomass feedstock.

The invention also relates to a power plant for on-demand producing electricity from non-fossil power sources and from a renewable lignocellulosic biomass feedstock.

BACKGROUND OF THE INVENTION

To date, and without considering the direct combustion of biomass, the main attempt to produce energy from plant biomass has been to produce biofuels such as bioethanol and other types of biofuels.

Such biofuels have appeared attractive, in particular, in trying to reduce the carbon dioxide emissions of automotive vehicles equipped with combustion engines, by replacing "fossil" fuels.

Fuels derived from plant biomass also emit carbon dioxide, but the carbon thus released was already present in the atmosphere.

Biofuels have thus appeared attractive from the point of view of carbon dioxide emissions.

In particular, the different technologies for the production of liquid biofuels—whether it is the transformation of lignocellulosic biomass by enzymatic hydrolysis or the thermochemical pathway—have low yields in terms of volume of production and in terms of energy balance. The overall energy balance of ethanol production by the conventional biochemical pathway can be penalized by the necessary energy consumption associated with the cultivation of dedicated plants, as well as by the energy consumption during the distillation operations.

In addition, in this sector, only the sugars contained in the plants are used for the production of biofuels and therefore for the production of energy.

Also, the costs of the enzymes do not permit a reaching of a sufficient economical balance—that is, continually affected in function of the price of the crude oil.

In the thermochemical pathway, all the components of the biomass are used for production of the biofuels and the overall energy balance might be better, but the overall economic balance remains very low.

Thus, no solution has emerged for industrial mass production of biofuels that would be satisfactory with regard to the different energy, economic and global ecological balances.

At the same time, it has become essential to develop all types of green or "clean" energy production, in particular green electricity, i.e., energies not using fossil fuels nor based on the nuclear industry.

These developments are also consistent with the evolution of the concept of motorized vehicles whose major trend in their mode of propulsion and their energy source consists nowadays in a total "electrification", or partial electrification through hybrid motorizations.

Such a lignocellulosic vegetable raw material is, for example, available in mass when one considers the lignocellulosic residues in logging and in the production of palm or palm trees, or the production of rice straw and cereal straw at large, or the bagasse in the sugar industry. In these two cases, a very abundant raw material is available for carrying out the process according to the invention which, to date, finds no profitable industrial use and under environmentally acceptable conditions for the production of energy, and for example for the production "in situ" of electricity.

Biomass is the unique direct and renewable storage facility of solar energy, and lignocellulosic waste feedstock does represent a more or less important part of this renewable non-fossil power source.

Moreover, for various reasons, it has also become necessary in the polymer industry to move towards a progressive replacement of products derived from the petroleum industry (i.e., from petrochemicals) by products derived from biomass (green chemistry).

In such a context, it has been proposed in US-A1-2012/0202260 a process for concurrent recovery of lignin derivatives and synthetic gas (syngas) from a lignocellulosic feedstock according to a "Hybrid bio refining and gasification of lignocellulosic feedstocks". However, after separation of the lignins and gasification of the "solids streams" and of the "Semi-solid and solid wastes" to produce syngas using conventional gasification equipment, it is proposed to process the syngas in order to produce various types of fuels such as Biodiesel, Butanol, Ethanol, Methanol, etc.

Syngas, or synthesis gas, is a fuel gas mixture consisting primarily of hydrogen, carbon monoxide, and very often some carbon dioxide.

Conversion of biomass to syngas is typically low-yield.

Electricity generation is the process of generating electric power from sources of primary energy. For electric utilities in the electric power industry, it is the first stage in the delivery of electricity to end users, the other stages being transmission, distribution, energy storage and recovery, using pumped-storage methods.

A characteristic of electricity is that it is not a primary energy freely present in nature in remarkable amounts and it must be produced. Production is carried out in power plants. Electricity is most often generated at a power station by electromechanical generators, primarily driven by heat engines fueled by combustion or nuclear fission, but also by other means such as the kinetic energy of flowing water and wind. Other energy sources include non-fossil power sources, such as solar photovoltaics and geothermal power.

Theoretically, syngas is composed of equimolar amounts of hydrogen $H_2$ and carbon monoxide $CO$ and carbon monoxide.

According to prior art techniques, the syngas obtained from gasification of lignocellulosic biomass is composed of impurities as dust, tar, halogen and alkali compounds with inorganic impurities, being hydrogen sulfide $H_2S$, ammonium $NH_3$, hydrogen chloride $HCl$, methane and other light hydrocarbon $C_2H_6$ contaminants of catalysts in downstream processes and specific cleaning operations and process are required to remove such contaminants.

A time consuming and very expensive gas cleaning is thus required to remove contaminants and provide a syngas within specifications for downstream processes and syngas utilization, while a gas conditioning system is required to eliminate main gas compounds and adjust the H2/CO ratio.

The main steps here are reforming of hydrocarbons, CO-shift to adjust the H2/CO ratio and removal of CO2.

After such time consuming and expensive gas treatment by cleaning and conditioning, syngas obtained from lignocellulosic biomass is chemically similar (CO, H2) to syngas derived from fossil sources and can replace its fossil equivalent in all applications.

Thus, there is a global need for a method for on-demand producing electricity from non-fossil power sources and from a renewable lignocellulosic biomass feedstock, and, in particular, wastes from agricultural production and from the forest industry, which makes it possible to valorize a part of the components of the lignocellulosic biomass in polymers industry, and the other components through the direct production of energy, for example production of electrical green or clean energy, with optimum energy, economic and ecological balances.

SUMMARY OF THE INVENTION

The invention proposes a method for on-demand producing electricity from non-fossil power sources and from a renewable lignocellulosic biomass feedstock, in an electricity power plant using several electricity production facilities comprising:
  i) at least a first facility for producing electricity from a non-fossil power source, the power source being chosen among wind power, and/or hydro power and/or solar power and/or geothermal power and/or tidal power; and
  at least a second facility using synthetic gas produced during the gasification step e) of a process for production of:
  non-oxidized, non-degraded and uncombined lignins with a controlled aliphatic hydroxyl content and controlled phenolic hydroxyl content; and
  synthetic gas
  the process comprising the following steps:
  a) extracting lignins and hemicellulose by putting at least one solid lignocellulosic raw material in the presence of a mixture, composed of at least water and formic acid, at atmospheric pressure under controlled conditions of temperature between 80° C. and 110° C., with a dilution ratio of the at least one solid lignocellulosic raw material/liquid mixture comprised between 1 and 15, and for a determined period of time, depending on the nature of the at least one lignocellulosic raw material;
  b) fractionating, at atmospheric pressure, the primary solid fraction (PSF) and the primary liquid fraction obtained at the end of the preceding extraction step a);
  c) recovering by evaporation-condensation of all or part of organic acids contained in the primary liquid fraction and obtaining an intermediate liquid fraction;
  d) separating the lignins from the intermediate liquid fraction, for example by precipitation by adding water, and obtaining a residual liquid fraction.
  e) gasifying at least part of the primary solid fraction and/or at least part of the residual liquid fraction for producing synthetic gas.
  According to other aspects of the method:
  the power plant comprises facilities for implementing the process;
  the lignocellulosic biomass based electricity producing facility comprises a synthetic gas storage facility;

The invention also proposes a power plant for on-demand producing electricity from non-fossil power sources and from a lignocellulosic renewable biomass feedstock, in a power plant using several electrical production facilities comprising at least:
  i) at least a first facility for producing electricity from a non-fossil power source, the power source being chosen among wind power, and/or hydro power and/or solar power and/or geothermal power and/or tidal power; and
  ii) at least a second facility using synthetic gas produced during a gasification step of several fractions from renewable lignocellulosic biomass feedstock obtained by the implementation of an organosolv process using a mixture composed of at least water and formic acid.

BRIEF DESCRIPTION OF THE DRAWINGS

The present invention will be described in conjunction with reference to the attached drawings in which.

DETAILED DESCRIPTION OF THE PREFERRED EMBODIMENTS

All biomass contains cellulose, hemicellulose and lignin in varying percentages, along with inorganic components which are the source of ash. Cellulose is a straight-chain polymer comprising anhydroglucopyranose joined with ether bonds. Hemicellulose is an amorphous polysaccharide containing sugar units which are branched and have varied sugar types. Lignin is the most complex constituent and is a polymer structure of phenylpropane units.

The most prominent constituent of biomass is lignocellulose, which consists of the non-starch, fibrous part of plant material. Cellulose, hemicellulose and lignin are the three main elements of lignocellulosic biomass. The cellulose-to-lignin ratio may vary and the proportion of cellulose and hemicellulose are directly related to the gaseous products yield, while the lignin content determines the pyrolysis oil in the product.

It has been identified that cellulose, hemicellulose and lignin fractions present in biomass feedstocks degrade at different temperature ranges during gasification. The variation in these constituents in biomass raw materials yields products with different calorific values. Gasification of pure cellulose does not yield water-soluble tars in the early stages.

This appears to be the consequence of the inhibition of the thermal polymerization by lignin during lignin/cellulose interactions in pyrolysis.

The rate of pyrolysis is thus directly related to cellulose fractions and inversely dependent upon lignin content in the feedstock.

Figure 1:
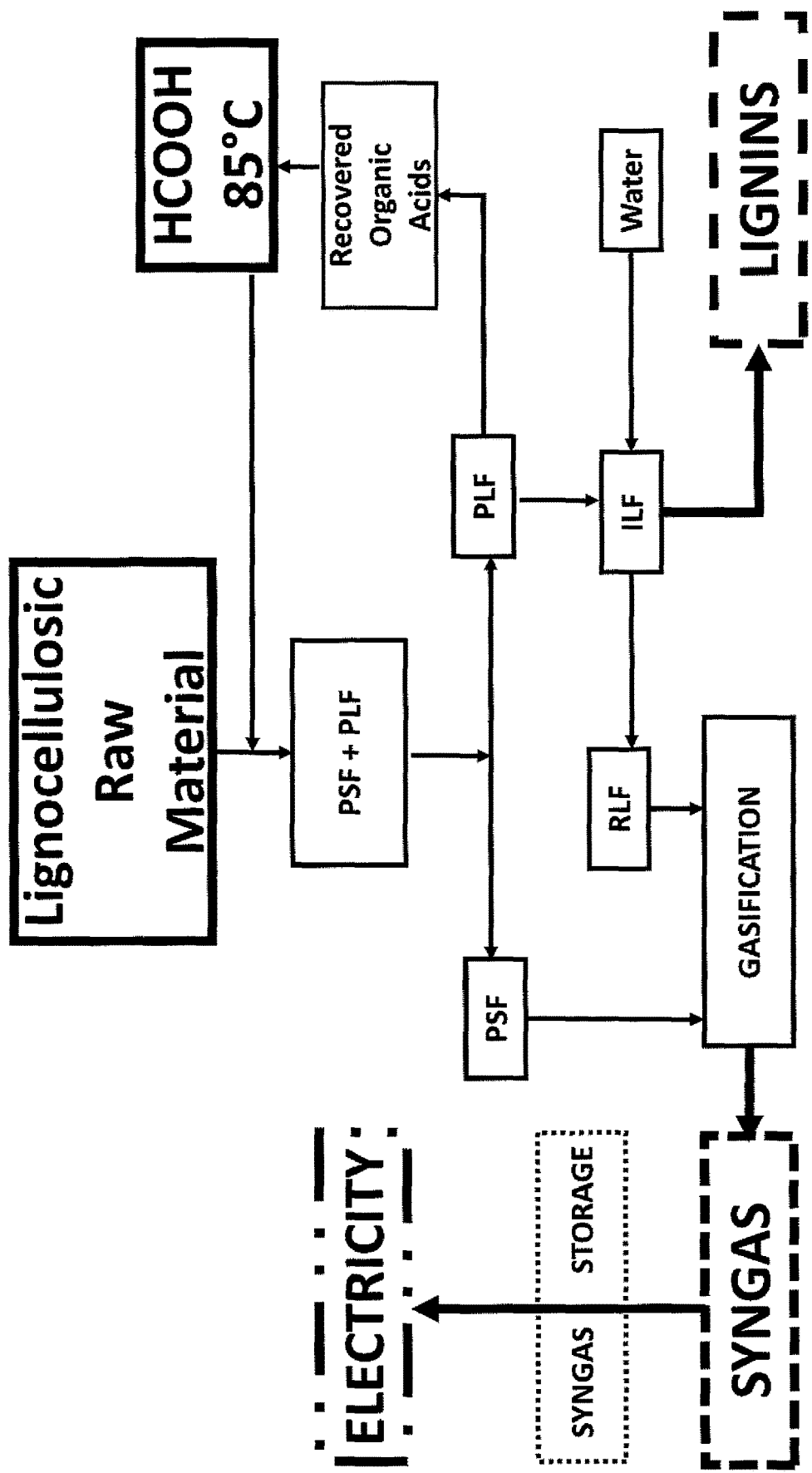
FIG. 1 schematically illustrates the main steps of an example of an acid based organosolv production process used for producing synthetic gas from lignocellulosic raw material.

A first example of extraction of lignins from a biomass Lignocellulosic Raw Material (LRM) using a mixture of water and formic acid (HCOOH) at low temperature and atmospheric pressure, as illustrated at FIG. 1, is as follows.

The first step consisted in preparing a solution of formic acid in water using a ratio in weight of 85% of formic acid and 15% of water.

In a second step, 30 grams of a dried sample of lignocellulosic feedstock (LRM) and 270 grams of the liquid mixture of formic acid in water have been introduced in a 500 milliliters glass reactor.

The liquid/solid mass ratio (Dilution ratio) was thus for example equal to 9/1.

In order to increase the contact surface between liquid and solid, the lignocellulosic raw material sample can be crushed.

At the ambient/atmospheric pressure and using an oil bath, the mixture of the acid/water solution and of the biomass lignocellulosic raw material sample is heated at a temperature between 80° C.-90° C.

This mixture is thus stirred using a mechanical stirrer with an Inox anchor to have a homogenous temperature.

Using a thermometer, the temperature has been stabilized at 85° C.

This extraction step is a very low energy consuming step (working at a low temperature under 110° C.).

At the end of this period of time of reaction, the content of the reactor has been cooled to the ambient temperature and it contains a solid fraction and a liquid fraction.

The content has then been filtered to separate the raw solid cellulose (constituting the Primary Solid Fraction PSF in the sense of the invention) from the liquid phase of the content constituting a first portion P1 of the Primary Liquid Fraction PLF in the sense of the invention.

The separated cellulose has been washed with formic acid and then pressed and filtered to remove in a liquid form a second portion P2 of the of the primary liquid fraction PLF in the sense of the invention.

First portion P1 and second portion P2 have then been mixed together to obtain the Primary Liquid Fraction PLF.

This primary liquid fraction PLF has further been concentrated under vacuum, preferably with a heating thereof between 40° C.-50° C., at a pressure of 100 milliBar.

This concentration phase has been maintained until the moment where the dry matter content was about 50% to 60% in weight.

At this stage, all parts of the formic acid contained in the primary liquid fraction PLF are recovered and separated to obtain an Intermediate Liquid Fraction (ILF) in the sense of the invention.

It appears that some other organics acids, such as acetic acid (CH3CO2H) could be generated or produced during the extraction step starting with formic acid in very small amounts. These other acids, after recovery are used in addition to the formic acid used for the above mentioned preparation of the water-acid mixture.

In order to separate or "extract" the lignins from the hemicellulose fraction in the intermediate liquid fraction ILF, warm Water has been added to the Intermediate Liquid Fraction ILF for reaching a liquid/solid mass ratio, for example equal to 4/1.

With a view to enhancing the separation of the lignins from the hemicellulose fraction, for example only, a high performance rotor/stator disperser has been used during a period of dispersion comprised between 2 and 3 minutes at a rotational speed greater than 15000 revolutions/minute.

At the end of this dispersion step, it has been processed with a filtration step to separate the lignins from the hemicellulose fraction and to obtain a Residual Liquid Fraction RLF in the sense of the invention.

The separated lignins have then been washed with warm water until a neutral pH of the filtrate has been reached.

The lignins have then been crushed and dried until reaching 94% of dry matter in weight, the drying temperature being not greater than 40° C.

At this stage the process has permitted to obtain:
A)—non-oxidized, non-degraded and uncombined lignins with a controlled aliphatic hydroxyl content and controlled phenolic hydroxyl content; and
B) a "compound" or mix comprising the primary solid fraction PSF and the residual liquid fraction RLF, that is available for direct gasification for production of syngas for production of energy, for example in the form of electricity.

This compound of PSF+RLF available for gasification is ready for gasification in the sense that:
i) It does not contain any lignins, or in a much reduced proportion, that have been identified as inhibitor of the gasification process;
ii) the gasification process is conducted on a compound containing only sugars;
iii) the sugars in the compound are in the most favorable H/C proportion for obtaining a synthetic gas having its optimal and maximum chemical and energetic efficiency, i.e., composed of equimolar amounts of carbon monoxide CO and of hydrogen H2;
iv) for producing electricity from the syngas obtained by gasification of the compound, syngas clean-up stages are no longer necessary, or are reduced to their minimum, as well as the problems inherent to the presence or ashes which are also avoided, or reduced when compared, for instance, with known electricity production processes using syngas obtained by direct gasification of the biomass (Biomass Gasification) or of material obtained from starting lignocellulosic raw material, for example through known organosolv processes, but containing lignins and/or hemicellulose.

In view of the above mentioned characteristics of the compound for gasification according to the above described and illustrated process, and of the characteristics and qualities of the synthetic gas obtained starting from this compound, for the efficient production of electricity, the synthetic gas obtained according to the process can be called "E2 Syngas" for "Electricity Efficient Syngas" or "Energy Efficient Syngas".

As illustrated in the attached drawings, before producing electricity or any other energy, such as steam for example, the syngas can be stored in a non-illustrated storage facility, preferably directly without any transformation nor any addition, in order to safeguard its high efficiency properties for producing electricity.

The above process for producing synthetic gas can be industrially implemented using a batch technique for the extraction step a), also including stirring of the content of each batch.

This is advantageous when compared with diffusion techniques that imply long and energy consuming extraction periods.

This is also advantageous when compared with diffusion techniques that imply specific "calibration" preparation steps of the Lignocellulosic Raw Material (LRM) by cutting, crushing, micronizing, etc. depending on the plant waste used as raw material.

Figure 2:
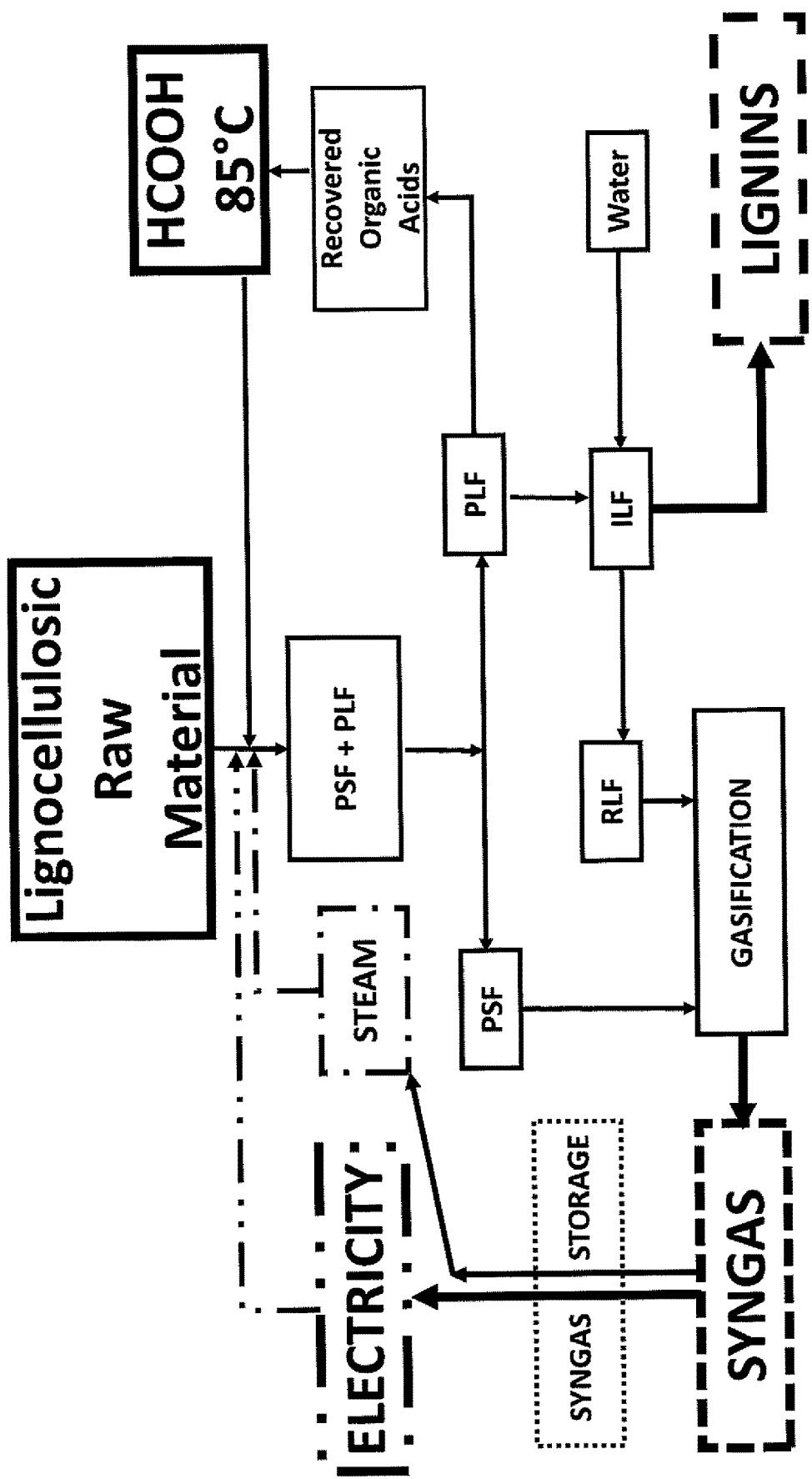
FIG. 2 is a figure analogous to FIG. 1 illustrating an improvement of the synthetic gas production process in an energetically autonomous way.

As illustrated at FIG. 2 the process that has been described in reference to FIG. 1 can be designed as an energetically autonomous process by using the electricity and/or any other energy (Such as steam) produced in using the E2 syngas as energy for producing the synthetic gas, and for instance during the extraction step using formic acid at 85° C.

The invention proposes to use the "E2 Syngas" as a non-fossil power source for producing electricity, i.e., for producing electricity from renewable lignocellulosic biomass feedstocks in a power plant and according to a method for on-demand producing electricity from Non-Fossil Power Sources (NFPS) and from a renewable lignocellulosic biomass feedstock (LRM).

Thus, the invention proposes a method for producing electricity from renewable power sources.

The invention proposes a method for on-demand continuously producing electricity from non-fossil power sources and from at least a lignocellulosic renewable biomass feedstock.

Figure 3:
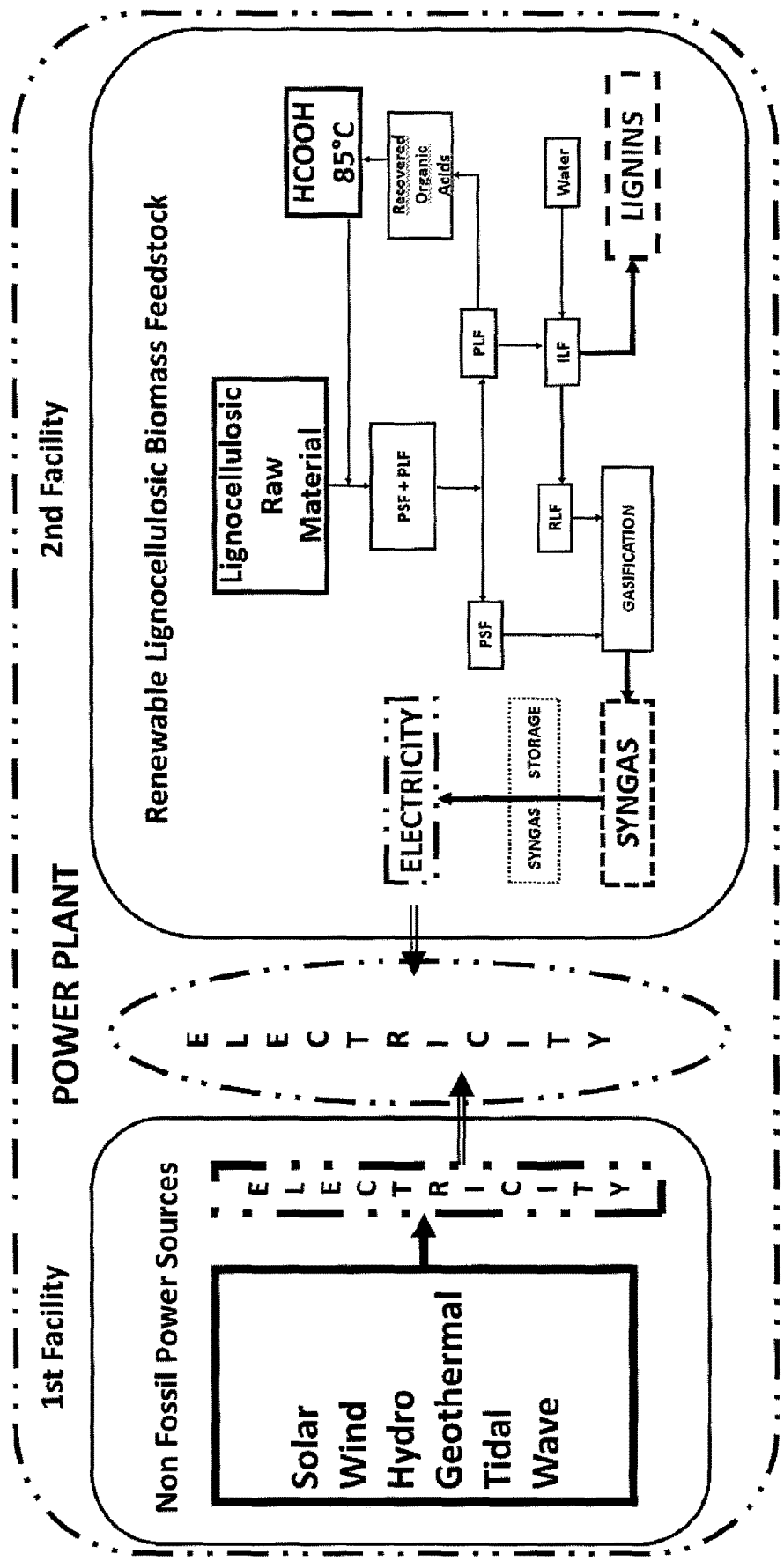
FIG. 3 is a schematic representation of a power plant according to the invention comprising a second facility for implementing the synthetic gas production process illustrated at FIG. 1.
Figure 4:
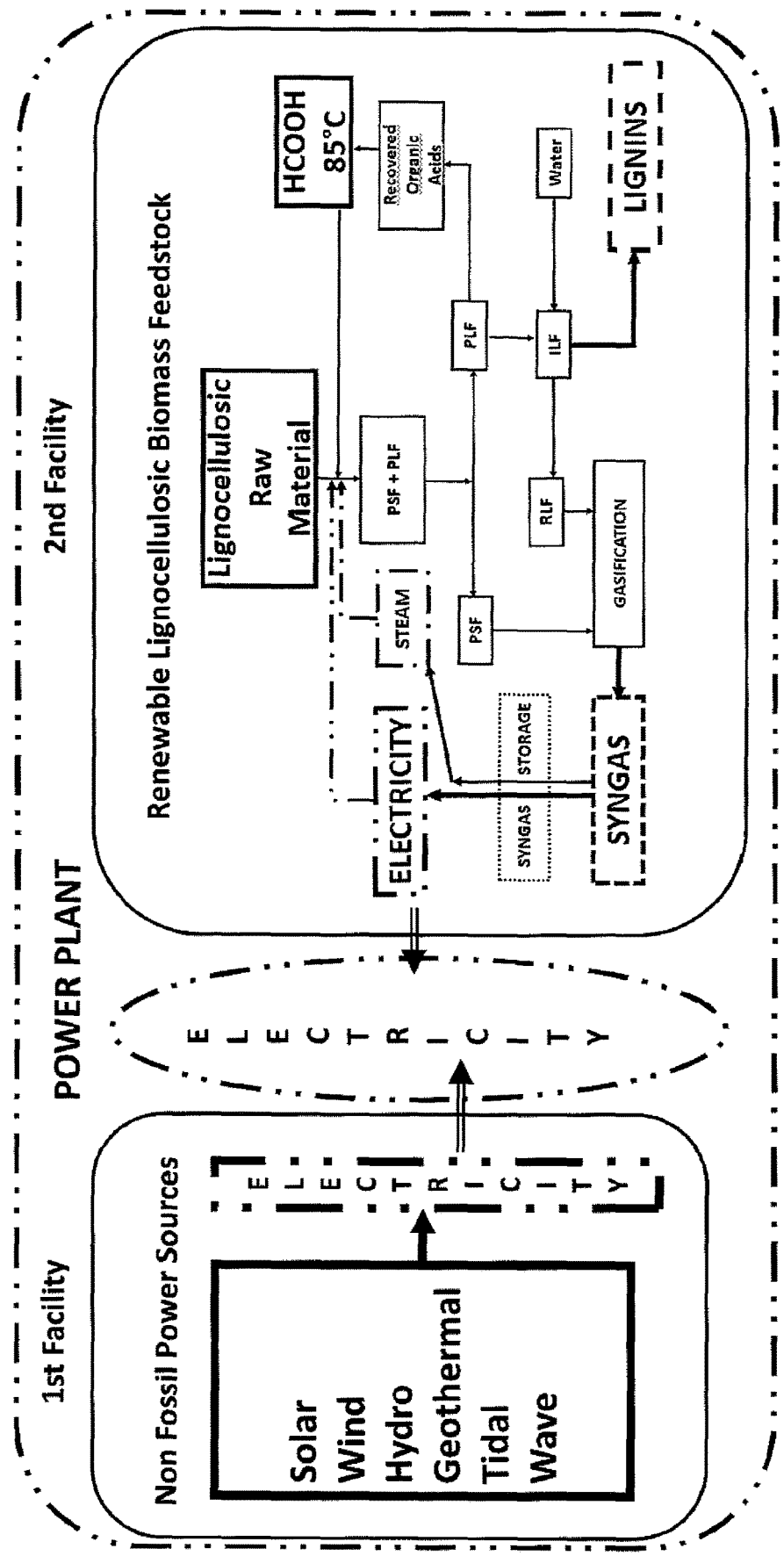
FIG. 4 is a schematic representation of a power plant according to the invention comprising a second facility for implementing the energetically autonomous synthetic gas production process illustrated at FIG. 2.

Such a method can be implemented in a factory or plant (POWER PLANT) as illustrated at FIG. 3 for producing electricity comprising at least:
- a first facility (1st Facility) for producing electricity using a Non-Fossil Power Source; and
- a second facility (2nd Facility) using Renewable Lignocellulosic Biomass Feedstock for producing E2 syngas obtained according to the above described process.

The renewable Non-Fossil Power Source(s) is (are) to be chosen among the Solar energy, the Wind power, the Wave power, the Tidal power, the Geothermal power and/or the Hydropower.

Beyond the above listed advantages in using E2 syngas obtained according to the above described process, the lignocellulosic raw material does appear as a "Backup fuel" or "Backup power source" for the production of electricity from Non-Fossil Power Sources (NFPS) when such sources are not available or not sufficiently available.

This is, for instance, the case during the night for solar energy, when there is not sufficient wind, when the tide is out, when a hydroelectric dam is "empty", etc.

This fuel or power source is a backup solution in two ways.

Firstly, the renewable lignocellulosic raw material can be easily stored at the 1st Facility.

Secondly, the E2 synthetic gas can easily be stored in any appropriate storage facility and dispatched on demand to the electricity production means of the 2nd Facility.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for on-demand producing electricity from non-fossil power sources and from a renewable lignocellulosic biomass feedstock, in an electricity power plant using several electricity production facilities comprising:
   i) at least a first facility for producing electricity from a non-fossil power source, said power source being chosen from among wind power, hydro power, solar power, geothermal power or tidal power; and
   ii) at least a second facility using synthetic gas produced during gasification step e) of a process for production of:
      non-oxidized, non-degraded and uncombined lignins with a controlled aliphatic hydroxyl content and controlled phenolic hydroxyl content; and
      synthetic gas,
   said process comprising the following steps:
      a) extracting lignins and hemicellulose by putting at least one solid lignocellulosic raw material in a presence of a mixture, composed of at least water and formic acid, at atmospheric pressure under controlled conditions of temperature between 80° C. and 110° C., with a dilution ratio of the at least one solid lignocellulosic raw material/liquid mixture comprised between 1 and 15, and for a determined period of time, depending on a nature of the at least one lignocellulosic raw material;
      b) fractionating, at atmospheric pressure, a primary solid fraction and a primary liquid fraction obtained at an end of extraction step a);
      c) concentrating the primary liquid fraction under vacuum at a second temperature between 40° to 50° C. until the primary liquid fraction comprises a dry matter content of 50 to 60 wt % and then separating at least part of organic acids contained in said primary liquid fraction and obtaining an intermediate liquid fraction;
      d) separating the lignins from said intermediate liquid fraction by diluting the intermediate liquid fraction with water and then filtering to recover the lignins, and obtain a residual liquid fraction;
      e) gasifying at least part of said primary solid fraction or at least part of said residual liquid fraction for producing synthetic gas.

2. The method according to claim 1, wherein said lignocellulosic biomass based electricity producing facility comprises a synthetic gas storage facility.

3. The method according to claim 1, further comprising:
   f) drying the lignin recovered in step d) at a temperature no greater than 40° C.

4. The method of claim 3, wherein step f) further comprises:
   crushing the lignin recovered in step d).

* * * * *